United States Patent [19]

Hamilton, Jr.

[11] Patent Number: 5,689,023
[45] Date of Patent: Nov. 18, 1997

[54] PROCESS FOR PREPARING STYRENE FROM ETHYLBENZENE USING A IRON OXIDE CATALYST

[75] Inventor: David Morris Hamilton, Jr., Houston, Tex.

[73] Assignee: Shell Oil Company, Houston, Tex.

[21] Appl. No.: 677,759

[22] Filed: Jul. 10, 1996

Related U.S. Application Data

[63] Continuation of Ser. No. 355,950, Dec. 14, 1994, abandoned.

[51] Int. Cl.$^6$ .............................. C07C 2/64; C07C 4/06; B01J 23/70; B01J 23/74
[52] U.S. Cl. .................. 585/444; 502/338; 502/517; 502/527
[58] Field of Search ........................... 585/444; 502/338

[56] References Cited

U.S. PATENT DOCUMENTS

| | | | |
|---|---|---|---|
| 1,368,748 | 2/1921 | Penniman, Jr. et al. | |
| 3,904,552 | 9/1975 | O'Hara | 252/458 |
| 4,006,090 | 2/1977 | Beck | 252/62.56 |
| 4,052,338 | 10/1977 | Riesser | 585/663 |
| 4,098,723 | 7/1978 | Riesser | 252/474 |
| 4,139,497 | 2/1979 | Castor et al. | 252/470 |
| 4,143,083 | 3/1979 | Riesser | 252/470 |
| 4,144,197 | 3/1979 | Riesser | 252/462 |
| 4,152,300 | 5/1979 | Riesser | 252/462 |
| 4,749,674 | 6/1988 | Dejaifve et al. | 502/304 |
| 4,758,543 | 7/1988 | Sherrod et al. | 585/444 |
| 4,857,498 | 8/1989 | Dejaifve et al. | 502/304 |
| 4,975,407 | 12/1990 | Dejaifve et al. | 502/338 |
| 5,023,225 | 6/1991 | Williams et al. | 502/309 |
| 5,047,382 | 9/1991 | Rudy et al. | 502/338 |
| 5,097,091 | 3/1992 | Kremer | 585/444 |
| 5,171,914 | 12/1992 | Hamilton, Jr. | 585/444 |
| 5,214,015 | 5/1993 | Farcasiu et al. | 502/222 |
| 5,364,827 | 11/1994 | Hettinger et al. | 502/338 |
| 5,580,839 | 12/1996 | Huffman et al. | 502/338 |

FOREIGN PATENT DOCUMENTS

| | | |
|---|---|---|
| 406633 A | 7/1989 | European Pat. Off. |
| 0 406 633 A2 | 6/1990 | European Pat. Off. |
| 1557143 | 4/1978 | United Kingdom. |

OTHER PUBLICATIONS

Wang, et al., Nonoxidative Dehydrogenation of Ethylbenzene Over TiO$_2$–ZrO$_2$ Catalysts, Journal of Catalysis 83, pp. 428–436 (1983).

Min–Dar Lee et al., Effects of Addition of Chromium, Manganese, or Molybenum to Iron Catalysts for Carbon Dioxide Hydrogention, Applied Catalysis, 72, pp. 267–281 (1991).

G. A. Somorjai, Modern Concepts in Surface Science and Heterogeneous Catalysis, J. Phys. Chem., pp. 1013–1023, (1990).

Nicholas J. Reeves and Stephen Mann, Influence of Inorganic and Organic Additives on the Tailored Synthesis of Iron Oxides, pp. 3875–3880 (date unknown).

Kenneth R. Hancock, Mineral Pigments, pp. 349–372 (date unknown).

M. Muhler, R. Schlogl, and G. Ertl, The Nature of the Iron Oxide–Based Catalysts for Dehydrogenation of Ethylbenzene to Styrene, Journal of Catalysis, 138, pp. 413–444 (1992).

Jianmin Zhao et al., Role of Molybdenum at the Iron Oxide Surface, Journal of Catalysis 148, pp. 194–197, (1994).

*Primary Examiner*—Glenn A. Caldarola
*Assistant Examiner*—J. Pasterczyk
*Attorney, Agent, or Firm*—Todd F. Volyn

[57] ABSTRACT

A process for preparing styrene from ethylbenzene in the presence of an iron oxide catalyst is presented. The catalyst is prepared from extruded alpha-FeOOH iron oxide particles derived from scrap metal via dehydration of a yellow alpha-Fe(OOH) intermediate via the Pennniman process and devoid of bound sulfate having a median size of at least 2 microns and results in improved catalyst activity.

2 Claims, No Drawings

5,689,023

PROCESS FOR PREPARING STYRENE FROM ETHYLBENZENE USING A IRON OXIDE CATALYST

This is a continuation of application Ser. No. 08/355,950 filed Dec. 14, 1994, now abandoned.

FIELD OF THE INVENTION

This invention relates to catalysts and processes for the dehydrogenation of hydrocarbons.

BACKGROUND OF THE INVENTION

Iron oxide based compositions are often employed as catalysts for the dehydrogenation of hydrocarbons. Iron oxides are found in a variety of forms including the so-called red, yellow, and black forms. Yellow iron oxide is usually geothite, which is the common form of hydrated iron oxide, FeOOH. Black iron oxide is magnetite, $Fe_3O_4$. The red form is the anhydrous form of iron oxide known as hematite, $Fe_2O_3$. The red form is typically prepared by calcining the yellow form to drive off water. When the red form is prepared in this manner, the resulting particles are typically acicular or needle shape. Acicular hydrated iron oxide can also be produced by direct precipitation. U.S. Pat. Nos. 3,364,277 and 3,703,593 teach the use of iron oxide to prepare dehydrogenation catalysts and are incorporated herein by reference.

The form, particulate structure, and other physical characteristics assumed by an iron oxide composition can affect the physical or chemical properties of the resulting catalyst. These properties are often manifested in catalyst performance as selectivity and activity enhancements or inhibitions. Broadly speaking, the selectivity of a catalyst is its ability to produce a particular product from among two or more possible reaction products. The activity of a catalyst is its overall ability to convert reactants to products. Ordinarily, an improvement in catalyst selectivity corresponds rather directly with a worsening of catalyst activity and vice versa.

This relationship between selectivity and activity presents difficulties because one seeking higher catalyst activity must generally plan on conducting more numerous or more involved separations since an increased number of chemical species is likely. On the other hand, one seeking improved selectivity must often accept smaller yields or more numerous recycle streams. Accordingly, the art could greatly benefit from a catalyst which did not exhibit this trade off between activity and selectivity when changes in one or the other parameter are sought.

SUMMARY OF THE INVENTION

The instant invention presents a method for improving the catalytic activity of an iron oxide catalyst without introducing a corresponding loss in selectivity.

In one aspect of this invention the catalyst is made from an iron-containing compound having large iron oxide particles.

In another aspect of this invention a process for preparing iron oxide dehydrogentation catalyst is presented in which an iron-containing compound having large particles of iron oxide is combined with a potassium containing compound and water, this mixture is then formed into a pellet, and the pellet is calcined.

In yet another aspect of this invention, a process for the preparation of styrene from ethylbenzene is presented. In this process, ethylbenzene is contacted with steam and a dehydrogenation catalyst having large particles of iron oxide.

In yet another aspect of this invention iron oxide dehydrogenation catalyst activity is improved by increasing the particle size of the iron oxide used therein.

DETAILED DESCRIPTION

This invention relates to a process for the preparation of a compound having the general formula:

Formula I wherein $R_1$ and $R_2$ each represent an alkyl, an alkenyl or a phenyl group or a hydrogen atom, by non-oxidative dehydrogenation of a compound having the general formula:

Formula II wherein $R_1$ and $R_2$ have the same meaning as in formula I, in which process a mixture comprising a compound of formula II and super-heated steam is contacted at elevated temperature with a catalyst comprising iron oxide and potassium oxide which has been prepared by combining an iron-containing compound and a potassium-containing compound to form a pellet, followed by calcination, wherein in preparing the catalyst there was used as at least part of the iron-containing compound from about 10 percent to about 100 percent by weight, basis $Fe_2O_3$, of iron oxide comprising enlarged particles. The iron oxide may comprise acicular, micaceous, or other configuration of iron oxide particles. The invention also relates to improved catalysts.

$R_1$ in formula II may reperesent a phenyl group carrying one or more methyl groups as substitutes. Preferably, $R_1$ is an unsubstituted phenyl group and $R_2$ is a hydrogen or a methyl group. Very good results have been obtained with ethylbenzene as the starting compound. The alkanes of formula II preferably have between about 2 to about 20 carbon atoms per molecule. It is even more preferred that they have between about 3 to about 8 carbon atoms such as in the case of n-butane and 2-methylbutane. The alkenes of formula II preferably have in the range of from about 4 to about 20 and particularly about 4 to about 8 carbon atoms per molecule. Examples include 1-butene (which can form 1,3-butadiene) and 2-methylbutane and 3-methyl-1-butene which both form isoprene. It is possible to convert n-butane with the present process via 1-butene into 1,3-butadiene and 2-methylbutane via ter.-amylenes into isoprenes.

Preferred compounds which can be produced according to this process are butadiene, alpha methyl styrene, and styrene. The use of the instant catalyst to convert ethylbenzene to styrene is particularly advantageous in that it is highly active and displays good selectivity.

A non-oxidative dehydrogenation is a dehydrogenation whereby no molecular oxygen is added. This is the type of dehydrogenation which occurs according to the process of this invention.

The term "selectivity" as used herein is the amount of compound of formula II that has been converted into compound of formula I divided by the total amount of compound of formula II that has been converted times 100. In the instant specification selectivities are typically measured at a standard rate of conversion of compound of formula II. For example, as used herein $S_{70}$ refers to the molar selectivity of ethylbenzene to styrene at a 70% molar conversion of ethylbenzene. The activity of a catalyst is inversely related to temperature. The more active the catalyst, the lower is the temperature that will be needed to obtain the same rate of conversion. Activities utilized in the instant specification are typically related to a given rate of conversion. For example, $T_{70}$ refers to the temperature at which a 70% molar conversion of ethylbenzene occurs.

The dehydrogenation process is suitably carried out using a molar ratio of steam to compound of formula II in the range of from about 2 to about 20 and preferably of from about 5 to about 13. The process is best carried out at a temperature in the range of from about 400° C. to about 750° C. Even more preferred is the temperature range from about 550° C. to about 650° C. The process may be carried out at atmospheric, super-atmospheric, or sub-atmospheric pressures. Atmospheric or sub-atmospheric pressures are preferred. It is also preferred that the process be carried out using a liquid hourly space velocity (LHSV) in the range of from about 0.1 to about 5.0 l/l/hr, using, for example, a tubular or radial flow reactor.

The catalyst may be used in the form of, for example, pellets, tablets, spheres, pills, saddles, trilobes, tetralobes and the like. The catalyst generally comprises about 5 to about 20 percent by weight of potassium oxide, from zero to about 10 percent by weight of oxides of one or more promoter metals selected from the group consisting of Sc, Y, La, rare earth, Mo, W, Ca, Mg, V, Cr, Co, Ni, Mn, Cu, Zn, Cd, Al, Sn, Bi, and mixtures thereof and the balance of $Fe_2O_3$. Preferred promoter metals are selected from the group consisting of Ca, Mg, Mo, W, Ce, Cr, and mixtures thereof. The term "oxide" as used herein encompasses not only the single oxides, such as ferric oxide, but also mixtures of oxides such as spinels and ferrites as well as binary and other oxide mixtures. Under reaction conditions these oxides may be present in part in the form of oxidic compounds such as carbonates and bicarbonates.

The catalysts of this invention are compounded in a variety of ways. Primarily, however, they are prepared by admixing iron-containing and potassium-containing compounds which are oxides or which convert to oxides upon calcining, forming this mixture into catalyst-sized particles and calcining at elevated temperature to form a durable particle. Promotor metal-containing compounds which are oxides or which also decompose to oxides upon calcination may be admixed with the iron-containing and potassium-containing compounds. The iron-containing, potassium-containing and promoter metal containing compounds can also be denoted as oxide-providing compounds and may comprise, for example, oxides, carbonates, bicarbonates, nitrates and the like.

The catalysts are prepared with procedures which are known in the art. One method is to mix together in a muller-mixer, for example, a mixture of oxides/hydroxides/ carbonates, etc., of iron, potassium and one or more optional promotor metals, adding a small amount of water, and extruding the paste to form small pellets, which are then dried at about 100° C. to about 300° C. and calcined at temperatures above 500° C., preferably between 700° C. and about 1000° C. Another method is to dissolve the components together, or to make a slurry and spray dry the resultant material to form a powder, calcine the powder into oxides, and then add sufficient water to form a paste to be subsequently extruded into pellets. The pellets can then be dried and calcined. Another method involves precipitation of those materials which are precipitatable such as iron, as the resultant hydroxides, partially dewatering the resultant precipitate, adding soluble salts, for example, of potassium and promotor metals like calcium and magnesium, and then subsequently extruding, drying and calcining the extrudate. A pellet mill or pellet press can be used to form pellets. A preferred method is to first dry mix the powdered components and then mix/mull these components with sufficient water to provide an extrudatable mass. After mulling, the mixture is extruded, dried and calcined.

Generally, after the components have been formed into a catalyst particle, the particle is calcined at elevated temperature to form a durable particle. The calcining temperature will be greater than about 500° C., preferably between about 700° C. and about 1000° C. Calcining atmospheres will generally be neutral (eg. nitrogen), or oxidizing, such as oxygen or preferably air.

The iron oxide-providing compound that is used in the preparation of the instant catalyst is characterized by its enlarged particle size. It is preferred that these enlarged iron oxides are synthesized so that particle sizes are at least quadrupled over those which are ordinarily used. It is most preferred that the catalyst be comprised of iron oxide particles at least about 2 microns along their longest dimension. One skilled in the art will recognize that particle size dimensions are made with reference to a statistical distribution of particle sizes. For example, the most preferred catalysts display a range of longest dimensions of which 2 microns is about the median of all particles.

Catalyst compositions comprised of such iron oxide particles typically are about 6° C. more active than are catalyst compositions having the same chemical structure and formulation but ¼ the iron oxide particle size. Furthermore, the increased activity is not accompanied by a decrease in selectivity. Thus, one can enhance the performance of iron oxide catalyst compositions by increasing the particle size of the iron oxide used therein.

Large particle iron oxides useful in this invention are most readily formulated from iron oxide derived from scrap iron via dehydration of a yellow α-FeOOH intermediate. This method is known in the art as the Penniman method as it is expressed in U.S. Pat. No. 1,368,748 which is incorporated herein by reference. One skilled in the art will readily appreciate that iron oxide particle size is adjusted through the precipitation time in the process.

The catalysts of this invention may also comprise any other iron compound, and can include yellow, black, and red iron oxides. Preferably, this includes an iron oxide-providing compound selected from the group consisting of geothite, hematite, magnetite, maghemite, lepidocrocite and mixtures thereof.

Catalysts formulated according to this invention generally display a higher median pore diameter and a larger pore volume than do the catalysts which are not prepared according to this invention. Typically, median pore diameters (MPD) are between about 2200 Å and 3000 Å, and pore volumes (PV) are between about 0.160 cm³/g and 0.221 cm³/g. Preferred catalyst compositions have MPDs between about 2500 Å and about 2955 Å. Most preferred catalyst compositions have MPDs greater than about 2600 Å. As used throughout this specification, median pore diameter is measured by the method of ASTM Standard D-4284-92, and pore volume is measured by the method of ASTM Standard D-4284-92.

The invention will be further described by the following nonlimiting examples:

EXAMPLES

Catalyst Preparation

In each of these examples, Penniman Red Iron Oxide (from Bayer AG, Germany) was used in catalyst formulation. This iron oxide is an α-FeOOH derived from scrap metal via dehydration of a yellow α-Fe(OOH) intermediate. Iron oxide particle size was regulated in accordance with U.S. Pat. No. 1,368,748.

The Table lists the physical characteristics of the catalysts and the approximate particle size of the iron oxide particles used to form the catalysts. In each case, the iron oxide was mixed with salts of promoters and water which was mixed in a muller-mixer. The resulting compositions were pelletized, dried at 170° C. for 1 hour, and calcined for 1 hour at 825° C. 105 ml of water were used for each kg of solids. The promoter salts included $K_2CO_3$, $CeCO_3$, $CaCO_3$, $(NH_4)_{10}W_{12}O_{41} \cdot 5H_2O$ and were added so that the following quantities of promoter were attained (expressed as mmole of promoter/mole of $Fe_2O_3$): 516 K, 66 Ce, 22 W, 36 Ca.

Catalyst Testing

Each of the catalysts prepared as outlined above were used in the preparation of styrene from ethylbenzene under isothermal conditions in a reactor designed for continuous operation. The conditions of the catalyst test were as follows: 100 cm³ of catalyst, 600° C. reactor temperature, LHSV of 0.65 measured in liters of ethylbenzene per liter of catalyst per hour, a steam to ethylbenzene molar ratio of 10:1, and a reactor pressure of 0.75 atmospheres.

The catalyst testing results are reported in terms of $T_{70}$ and $S_{70}$ where $T_{70}$ is the temperature required for a given catalyst to convert 70% of the ethylbenzene feed to products and $S_{70}$ is the molar selectivity to product styrene. Catalyst testing results are also shown in the Table.

This example, as demonstrated by the results listed in the Table, shows that catalysts made from iron oxide having large particle dimensions demonstrate improved activity in dehydrogenation reactions without noticeable effect on reaction selectivity. The results also show that greater catalyst made according to this invention which display larger MPDs exhibit enhanced activity without a loss in selectivity.

| Catalyst | Approx. Particle Size (Microns) | Bulk Density g/cm³ | Surface Area m²/g | Pore Volume cm³/g | Median Pore Diameter Å | Activity $T_{70}(c)$ | Selectivity $S_{70}(\%)$ |
|---|---|---|---|---|---|---|---|
| I | .5 | 1.33 | 2.31 | .1853 | 2267 | 602.4 | 95.0 |
| II | .5 | 1.38 | 1.63 | .1665 | 2395 | 603.7 | 95.2 |
| III | .5 | 1.38 | 1.39 | .1606 | 2815 | 606.3 | 95.3 |
| IV | 1 | 1.25 | 2.39 | .2213 | 2761 | 602.7 | 94.2 |
| V | 1 | 1.37 | 1.81 | .1796 | 2574 | 600.6 | 94.3 |
| VI | 1 | 1.36 | 1.33 | .1660 | 2867 | 603.2 | 95.1 |
| VII | 2 | 1.35 | 2.13 | .1780 | 2618 | 599.4 | 95.0 |
| VIII | 2 | 1.35 | 1.86 | .1818 | 2929 | 598.2 | 95.0 |
| IX | 2 | 1.39 | 1.67 | .1685 | 2955 | 597.4 | 95.3 |

What is claimed is:

1. In a method of preparing styrene from ethylbenzene using an extruded iron oxide catalyst, the improvement consisting of increasing the catalytic activity in said process by selecting for use in said catalyst, iron oxide produced from alpha-FeOOH derived from scrap metal via dehydration of a yellow alpha-Fe(OOH) intermediate and having particles with a particle size of at least about 2 microns in at least a median number of particles and wherein said iron oxide is devoid of bound sulfate.

2. The method of claim 1 wherein the median of particles comprising said iron oxide are at least about 2 microns along their longest dimension.

* * * * *